United States Patent [19]

Kishino et al.

[11] 4,013,793
[45] Mar. 22, 1977

[54] COMBATING PESTS WITH O-ETHYL-S-PROPYL-THIONOTHIOL OR DITHIOPHOSPHORIC ACID PHENYL OR NAPHTHYL ESTERS

[75] Inventors: Shigeo Kishino, Tokyo; Akio Kudamatsu, Kanagawa; Iwao Takase, Tokyo; Kozo Shiokawa, Kanagawa; Shin-ichi Yamaguchi, Tokyo, all of Japan

[73] Assignee: Nihon Tokushu Noyaku Seizo Kabushiki Kaisha, Tokyo, Japan

[22] Filed: Apr. 25, 1975

[21] Appl. No.: 571,881

Related U.S. Application Data

[62] Division of Ser. No. 471,081, May 17, 1974, Pat. No. 3,898,334, which is a division of Ser. No. 123,087, March 10, 1971, Pat. No. 3,825,636.

[30] Foreign Application Priority Data

Mar. 13, 1970 Japan ............... 45-20845

[52] U.S. Cl. ............... 424/210; 424/216; 424/217; 424/218; 424/225
[51] Int. Cl.² ............... A01N 9/36
[58] Field of Search .......... 424/210, 216, 217, 218, 424/225

[56] References Cited

UNITED STATES PATENTS

| 3,732,341 | 5/1973 | Sirreaberg | 260/950 |
| 3,898,334 | 8/1975 | Kuhno et al. | 424/225 |

FOREIGN PATENTS OR APPLICATIONS

| 255,279 | 2/1963 | Australia | 260/954 |
| 98,101 | 2/1964 | Denmark | 260/949 |

*Primary Examiner*—Leonard Schenkman
*Attorney, Agent, or Firm*—Burgess, Dinklage & Sprung

[57] ABSTRACT

O-ethyl-S-n-propyl-dithiophosphoric acid phenyl or naphthyl esters, i.e. O-ethyl-S-n-propyl-O- or S—optionally substituted phenyl or naphthyl-phosphorothionothiol- or dithiolates, of the formula

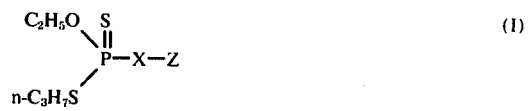

in which
X is an oxygen or sulfur atom, and
Z is a group of the formula

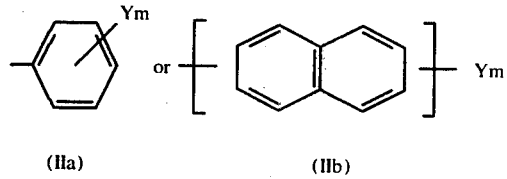

(IIa)       (IIb)

Y is a halogen atom or a lower alkyl, lower alkoxy, lower alkylmercapto, lower alkylsufinyl, nitro, cyano or phenyl group, and
m is 0, 1, 2 or 3,
which possess insecticidal, acaricidal and nematocidal properties.

9 Claims, No Drawings

COMBATING PESTS WITH O-ETHYL-S-PROPYL-THIONOTHIOL OR DITHIOPHOSPHORIC ACID PHENYL OR NAPHTHYL ESTERS

This is a division of application Ser. No. 471,081, filed May 17, 1974, now U.S. Pat. No. 3,898,334, which is a division of Ser. No. 123,087, filed Mar. 10, 1971, now U.S. Pat. No. 3,825,636, issued July 23, 1974.

The present invention relates to and has for its objects the provision of particular new D-ethyl-S-n-propyldithiophosphoric acid phenyl or naphthyl esters, i.e., O-ethyl-S-n-propyl-O- or S-optionally substituted phenyl or naphthyl-phosphorothionothiol- or dithiolates, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

In an agriculture, especially the cultivation of rice-plants, the damage caused by larvae of insects belonging to the Lepidoptera, such as the rice stem borer (*Chilo suppressalis*) and yellow rice borer (*Tryporyza incertulas*), and mites is a serious problem.

Much research has been directed to the control of these harmful creatures but only several pesticides among commercially available pesticides are effective against them; almost all of these pesticides comprise organic phosphorous compounds. Further, since the same insecticides have been used in great amounts, there has been a tendency for the harmful insects to acquire resistance to these insecticides.

The present invention provides phosphoric acid esters of the general formula:

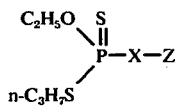

in which
X is an oxygen or sulfur atom, and
Z is a group of the formula

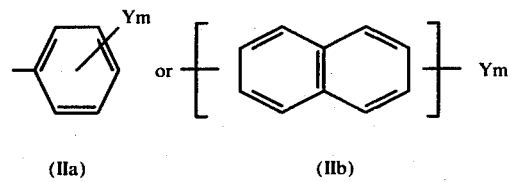

(IIa)    (IIb)

in which
Y is a halogen atom or a lower alkyl, lower alkoxy, lower alkylmercapto, lower alkylsulfinyl, nitro, cyano or phenyl group, and
m is 0, 1, 2 or 3.

Although Y may be a fluorine or iodine atom, the preferred halogens are chlorine and bromine. Preferred lower alkyl and alkoxy groups include those with an alkyl moiety of 1 to 4 carbon atoms, namely methyl, ethyl, n- and iso-propyl and n-, iso-, sec- and tert-butyl.

When the compounds of this invention are compared with known compounds having analogous structures and compounds having similar directions of biological activity, the compounds of this invention are characterized by substantially improved effects and very low toxicity to warm-blooded animals and hence, they are of great utility.

The compounds of this invention can be used for controlling harmful insects of a broad range such as harmful sucking insects, biting insects and plant parasites.

They are especially effective as pesticides against insects harmful to agriculture, such a insects belonging to the Coleoptera, Lepidoptera, Aphidae, Orthoptera, Isoptera and Acarina as well as Nematodes living on plant and soil, and they can be used as agents for protecting plants from such creatures.

The compounds of this invention exhibit a more pronounced insecticidal activity than analogous compounds against insects belonging to the Lepidoptera, whose control has been difficult by the conventional insecticides. Further, they exhibit a very high insecticidal activity against insects which have acquired resistance to the phosphorous-compound insecticides of the prior art. Still further, they are effective for controlling rice stem borers. The compounds of the invention have a very low toxicity and, in particular, do not exhibit such an acute toxicity to humans as is possessed by parathion and methylparathion. Nevertheless, the insecticidal activity of the compounds of this invention is comparable or superior to that of parathion and, therefore, they can safely be used as agricultural chemicals.

The present invention also provides a process for the preparation of a compound of the formula (I) in which (a) a thionophosphoric acid diester halide of the general formula

is reacted with a mercaptan of the general formula

or (b) a compound of the general formula

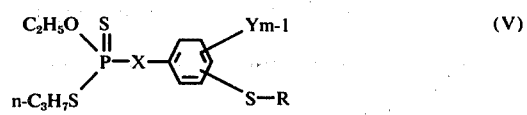

is reacted with a suitable oxidizing agent, preferably hydrogen peroxide,
in which formulae
Hal is a halogen, preferably a chlorine, atom,
M is a hydrogen atom or an alkali metal atom,
R is a lower alkyl group, and
X, Y, Z and m have the meaning stated above.

As suitable thionophosphoric acid diester monohalides of the formula (III), the following may be cited:

O-ethyl-O-phenyl-thionophosphoric acid chloride,

O-ethyl-O-(2-chlorophenyl)-thionophosphoric acid chloride,
O-ethyl-O-(4-chlorophenyl)-thionophosphoric acid chloride,
O-ethyl-O-(4-bromophenyl)-thionophosphoric acid chloride,
O-ethyl-O-(2,4-dichlorophenyl)-thionophosphoric acid chloride,
O-ethyl-O-(2,4-dibromophenyl)-thionophosphoric acid chloride,
O-ethyl-O-(2,4,5-trichlorophenyl)-thionophosphoric acid chloride,
O-ethyl-O-(2,4,6-trichlorophenyl)-thionophosphoric acid chloride,
O-ethyl-O-(2,5-dichloro-4-bromophenyl)-thionophosphoric acid chloride,
O-ethyl-O-(2,4-dimethylphenyl)-thionophosphoric acid chloride,
O-ethyl-O-(3,4-dimethylphenyl-thionophosphoric acid chloride,
O-ethyl-O-(4-tert-butylphenyl)-thionophosphoric acid chloride,
O-ethyl-O-(2-chloro-4-tert-butylphenyl)-thionophosphoric acid chloride,
O-ethyl-O-(3,5-dimethyl-4-chlorophenyl)-thionophosphoric acid chloride,
O-ethyl-O-(2,4-dichloro-6-methylphenyl)-thionophosphoric acid chloride,
O-ethyl-O-(4-methoxyphenyl)-thionophosphoric acid chloride,
O-ethyl-O-(4-methylmercaptophenyl)-thionophosphoric acid chloride,
O-ethyl-O-(2-methyl-4-methylmercaptophenyl)-thionophosphoric acid chloride,
O-ethyl-O-(3-methyl-4-methylmercaptophenyl)-thionophosphoric acid chloride,
O-ethyl-O-(4-methylsulfinylphenyl)-thionophosphoric acid chloride,
O-ethyl-O-(3-methyl-4-methylsulfinylphenyl)-thionophosphoric acid chloride,
O-ethyl-O-(2-nitrophenyl)-thionophosphoric acid chloride,
O-ethyl-O-(4-nitrophenyl)-thionophosphoric acid chloride,
O-ethyl-O-(3-chloro-4-nitrophenyl)-thionophosphoric acid chloride,
O-ethyl-O-(3-nitro-4-chlorophenyl)-thionophosphoric acid chloride,
O-ethyl-O-(2-chloro-4-nitrophenyl)-thionophosphoric acid chloride,
O-ethyl-O-(3-methyl-4-nitrophenyl)-thionophosphoric acid chloride,
O-ethyl-O-(4-cyanophenyl)-thionophosphoric acid chloride,
O-ethyl-O-(4-biphenyl)-thionophosphoric acid chloride,
O-ethyl-O-(2-chloro-4-biphenyl)-thionophosphoric acid chloride,
O-ethyl-O-(alpha-naphthyl)-thionophosphoric acid chloride,
O-ethyl-O-(beta-naphthyl)-thionphosphoric acid chloride,
O-ethyl-O-(1-bromo-beta-naphthyl)-thionophosphoric acid chloride,
O-ethyl-O-(2,4-dichloro-alpha-naphthyl)-thionophosphoric acid chloride,
O-ethyl-S-phenyl-thionophosphoric acid chloride,
O-ethyl-S-(4-chlorophenyl)-thionophosphoric acid chloride,
O-ethyl-S-(2,5-dichlorophenyl)-thionophosphoric acid chloride, and
O-ethyl-S-(4-methylphenyl)-thionophosphoric acid chloride.

In process variant (a), the reaction is preferably effected in a solvent, which term herein includes a mere diluent. Any inert solvent may be used for this purpose, for example water, aliphatic and aromatic hydrocarbons which may be halogenated, such as methylene chloride, di-, tri- and tetrachloroethylenes, chloroform, carbon tetrachloride, benzine, benzene, chlorobenzene, toluene and xylene; ethers such as diethyl ether, di-n-butyl ether, diotane and tetrahydrofuran; low-boiling aliphatic ketones and nitriles such as acetone, methylethylketone, methylisopropylketone, methylisobutylketone, acetonitrile and propionitrile; and low-boiling aliphatic alcohols such as methanol, ethanol and isopropanol.

The reaction of process variant (a) may be carried out in the presence of an acid-binder according to need, usually when M is a hydrogen atom. Suitable acid-binders are hydroxides, carbonates, bicarbonates and alcoholates of alkali metals and tertiary organic bases such as triethylamine, dimethylaniline and pyridine. When the reaction is carried out in the absence of acid-binder, the intended product of high purity can be obtained in high yield by first forming an alkali metal salt of n-propylmercaptan and then reacting the salt with the phosphoric acid diester mono-halide.

The reaction of process variant (a) may be effected at temperatures of a fairly broad range, but generally the reaction is carried out at from −20° C to the boiling point of the reaction mixture, preferably from 0° to 100° C.

The process variant (b) is, of course, suitable for the preparation only of those compounds of the formula (I) in which Z is a phenyl group substituted by an alkylsulfinyl group, with $m$ being, therefore, at least 1.

The reaction of process variant (b) is preferably effected in a solvent, for example one of those mentioned above, and the oxidant is conveniently aqueous hydrogen peroxide.

The reaction may be effected at temperatures within a fairly broad range, but preferably the reaction is effected at 0° to 100° C.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations, preparations or compositions, e.g. conventional pesticide formulations, preparations or compositions such as solutions, emulsions, suspensions, emulsifiable concentrates, wettable powders, soluble powders, oils, aerosols, pastes, fumigating powders, dusting powders, granules, pellets and tablets, etc.. These are formulated or prepared in known manner, for instance by mixing the active compounds with conventional pesticide dispersible liquid or solid diluent, carriers or extenders optionally with the use of carrier vehicle assistants, e.g, conventional pesticide surface-active agents, including emulsifying agents adhesive agent and/or dispersing agents, whereby, for example, in the case where water is used as diluent, organic solvents and/or surfactants may be added as auxiliary solvents. The following may be chiefly considered for use as conventional carrier vehicles for this purpose: aerosol propellants which are gaseous at normal temperatures and pessures, such as freon; inert dispersible liquid diluent carriers, including inert organic solvents, such as aromatic hydrocarbons (e.g. benzene, toluene, xylene, aromatic naphtha, dimethyl naphthalene, etc.), halogenated, especially chlorinated aromatic hydrocarbons (e.g. chlorobenzenes etc.), aliphatic hydrocarbons (e.g. benzine, cyclohexane, paraffins, petroleum fractions), chlorinated aliphatic hydrocarbons (e.g. methylene chloride, ethylene chloride, etc.), alcohols (e.g. methanol, ethanol, propanol, butanol, etc.), amines (e.g. ethanolamine, etc.), ethers, ether-alcohols, (e.g. glycol monomethyl ether, etc.), amides (e.g. dimethyl formamide, etc.) sulfoxides (e.g. dimethyl sulfoxide, etc.), ketones (e.g. acetone, methylethyl ketone, cyclohexanone, etc.) and/or water; as well as inert dispersible finely divided solid carriers, such as ground natural minerals (e.g. clays, talc, pyrophyllite, mica, gypsum, calcite, vermiculite, dolomite, apatite, calucium or magnesium lime, diatomaceous earth, inorganic salts i.e. calcium carbanate, pumice, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic and/or cationic emulsifying agents, (e.g. polyethyleneoxide esters of fatty acids, polyethylene oxide ethers of fatty alcohols, alkyl sulfonates, aryl sulfonates, alkyl dimethyl benzyl ammonium chloride, etc., and especially alkyl arylpolyglycol ethers, magnesium stearate, sodium oleate, etc.): and/or dispersing agents, such as lignin, sulfite waste liquors, methyl cellulose, etc..

Such active compounds may be employed along or in the form of mixtures with one another and/or with such solid and/or liquid dispersible carrier vehicles, optionally with the use of carrier vehicle assistants and/or with other known compatible active agents, especially plant protection agents, such as other insecticides, acaricides, nematocides, fungicides, bactericides, herbicides, rodenticides, fertilizers or plant growth-regulating agents, etc., if desired, or in the form of particular dosage preparations for specific application made therefrom, such as solutions, emulsions, suspensions, powders, pastes, and granules which are thus ready for use.

As concerns commercially marketed formulations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20%, preferably 0.001–5%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.001–95%, by weight of the mixture.

The amount of active compound applied per unit area is usually about 150 to 10000 grams, preferably 400 to 6000 grams of active compound per hectare. However, in special cases, it may be possible to use more or less, sometimes such variations may be required.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microsn, or even less, i.e. mist form, for example by airplane crop spraying techniques. Only up to at most about a few liters/hectare are needed, and often amounts only up to about 150 to 10000g/hectare preferably 400 to 6000g/hectare, are sufficient. In this process it is possible to use highly concentrated liquid compositions with said liquid carrier vehicles containing from about 20 to about 95% by weight of active compound or even the 100% active substance alone, e.g. about 20–100% by weight of the active compound.

Furthermore, the present invention contemplates methods of selectively killing, combating or controlling pests, e.g. arthropods, i.e. insects and acarids, and more particularly methods of combating at least one of insects and acarids which comprises applying to at least one of correspondingly (a) such insects, (b) such acarids, and (c) the corresponding habitat thereof, i.e. the locus to be protected, a correspondingly combative or toxic amount, i.e. an arthropodicidally, especially insecticidally or acaricidally, effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

20.5 g of the sodium salt of n-propylmercaptan are suspended in 100 ml of acetonitrile, and 61 g of O-ethyl-O-(2,4-dichlorophenyl) thionophosphoric acid chloride are added to the suspension dropwise at 5°–10° C with vigorous agitation. The temperature is gradually raised to 70° C, and at this temperature the reaction is carried out for 3 hours.

Acetonitrile is removed from the reaction mixture by distillation and the residue is dissolved in benzene, washed with water and 1% sodium carbonate and dried over anhydrous sodium sulfate. Distillation of the benzene gives 55 g of O-ethyl-O-(2,4-dichlorophenyl)-S-n- propyl-phosphorothionothiolate of the following formula:

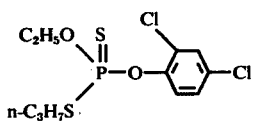
(4)

The product has a boiling point of 164°–167° C under 0.18 mmHg and a refractive index $n_D^{20}$ of 1.5698. The compound is hereinafter identified as compound No. 4.

EXAMPLE 2

16 g of n-propylmercaptan are added to 4.8 g of sodium metal in 150 ml of toluene, and heating is effected to dissolve the sodium. After cooling of the mixture, 56.6 g of O-ethyl-O-(4-methylmercapto-phenyl) thionophosphoric acid chloride are added thereto dropwise, and the temperature is gradually raised to 80° C at which the reaction is carried out for 5 hours. The reaction mixture is washed with water and 1% sodium carbonate and dried over anhydrous sodium sulfate. Distillation of toluene gives 53 g of O-ethyl-O-(4-methyl-mercapto-phenyl)-S-n-propylphosphorothionothiolate of the following formula:

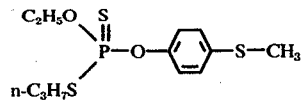
(17)

The product has a boiling point of 155°–158° C under 0.1 mmHg and a refractive index $n_D^{20}$ of 1.5859. The compound is hereinafter identified as compound No. 17.

EXAMPLE 3

32 g of O-ethyl-O-(4-methylmercapto-phenyl)-S-n-propylphosphorothionothiolate are dissolved in 150 ml of methanol. Several drops of 50% sulfuric acid are added to the solution, and 12 g of 30% aqueous hydrogen peroxide are added thereto dropwise at 5°–10° C. The mixture is agitated for 1 hour and further agitation is conducted at 40° C for 3 hours. A major portion of the methanol is removed by distillation and the residue is dissolved in benzene, washed with water and 1% sodium carbonate, and dried over anhydrous sodium sulfate. Distillation of benzene gives 30 g of O-ethyl-O-(4-methylsulphinyl-phenyl)-S-n-propylphosphorothionothiolate of the following formula:

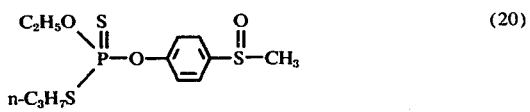
(20)

After the product as been subjected to column chromatography with active alumina, it exhibits a refractive index $n_D^{20}$ of 1.5820. The compound is hereinafter identified as compound No. 20.

EXAMPLE 4

The following compounds may be prepared by methods analogous to those described in Examples 1, 2 and 3.

Table 1

$$\begin{array}{c} C_2H_5O \\ \diagdown \\ P-X-Z \\ \diagup \\ n\text{-}C_3H_7S \end{array} \quad (I)$$

| Compound No. | X | Z | Boiling Point or Melting Point | Refractive Index |
|---|---|---|---|---|
| 1 | O | —C₆H₅ | b.p. 128–131° C/0.05 mmHg | $n_D^{20}$ 1.5490 |
| 2 | O | 2-Cl-C₆H₄ | b.p. 136–138° C/0.08 mmHg | $n_D^{20}$ 1.5620 |
| 3 | O | 4-Cl-C₆H₄ | b.p. 158–162° C/0.15 mmHg | $n_D^{20}$ 1.5601 |
| 5 | O | 2,4,5-Cl₃-C₆H₂ | b.p. 150–152° C/0.05 mmHg | $n_D^{20}$ 1.5790 |
| 6 | O | 2,4,6-Cl₃-C₆H₂ | b.p. 145–148 C/0.05 mmHg | $n_D^{20}$ 1.5737 |
| 7 | O | 4-Br-C₆H₄ | b.p. 130–132° C/0.05 mmHg | $n_D^{20}$ 1.5758 |

Table 1-continued $$\begin{array}{c} C_2H_5O \quad S \\ \diagdown \parallel \\ P-X-Z \\ \diagup \\ n\text{-}C_3H_7S \end{array} \qquad (I)$$

| Compound No. | X | Z | Boiling Point or Melting Point | Refractive Index |
|---|---|---|---|---|
| 8 | O | Br—C₆H₃(Br)— | | |
| 9 | O | Cl—C₆H₂(Br)(Cl)— | b.p. 148–152° C/0.07 mmHg | $n_D^{20}$ 1.5972 |
| 10 | O | CH₃—C₆H₃—CH₃ | b.p. 134–138° C/0.07 mmHg | $n_D^{20}$ 1.5484 |
| 11 | O | —C₆H₃(CH₃)(CH₃) | b.p. 128–130° C/0.07 mmHg | $n_D^{20}$ 1.5530 |
| 12 | O | —C₆H₄—C₄H₉—tert | b.p. 140–143° C/0.05 mmHg | $n_D^{20}$ 1.5391 |
| 13 | O | Cl—C₆H₃—C₄H₉—tert | | $n_D^{20}$ 1.5412 |
| 14 | O | —C₆H₂(CH₃)(Cl)(CH₃) | b.p. 130–132° C/0.1 mmHg | $n_D^{20}$ 1.5567 |
| 15 | O | Cl—C₆H₂(Cl)(CH₃)— | b.p. 130–135° C/0.2 mmHg | $n_D^{20}$ 1.5630 |
| 16 | O | —C₆H₄—OCH₃ | b.p. 155–158° C/0.1 mmHg | $n_D^{20}$ 1.5561 |
| 18 | O | —C₆H₃(CH₃)—SCH₃ | b.p. 159–160° C/0.1 mmHg | $n_D^{20}$ 1.5834 |
| 19 | O | CH₃—C₆H₃—SCH₃ | b.p. 155–156° C/0.1 mmHg | $n_D^{20}$ 1.5788 |
| 21 | O | —C₆H₃(CH₃)—S(O)—CH₃ | | $n_D^{20}$ 1.5810 |
| 22 | O | NO₂—C₆H₄— | | |
| 23 | O | —C₆H₄—NO₂ | b.p. 145–150° C/0.05 mmHg | $n_D^{20}$ 1.5660 |

Table 1-continued $$\underset{n\text{-}C_3H_7S}{\overset{C_2H_5O}{\diagdown}}\underset{\|}{\overset{S}{P}}-X-Z \qquad (1)$$

| Compound No. | X | Z | Boiling Point or Melting Point | Refractive Index |
|---|---|---|---|---|
| 24 | O | 2-Cl-4-NO$_2$-C$_6$H$_3$- | | $n_D^{20}$ 1.5640 |
| 25 | O | 2-Cl-3-NO$_2$-C$_6$H$_3$- | | |
| 26 | O | 2-Cl-4-NO$_2$-C$_6$H$_3$- | | $n_D^{20}$ 1.5700 |
| 27 | O | 2-CH$_3$-4-NO$_2$-C$_6$H$_3$- | | $n_D^{20}$ 1.5617 |
| 28 | O | 4-Cl-C$_6$H$_4$- | b.p. 140–144° C/0.08 mmHg | $n_D^{20}$ 1.5677 |
| 29 | O | 4-C$_6$H$_5$-C$_6$H$_4$- | | $n_D^{20}$ 1.6043 |
| 30 | O | 3-Cl-4-C$_6$H$_5$-C$_6$H$_3$- | | $n_D^{20}$ 1.6121 |
| 31 | O | 1-naphthyl | b.p. 170–173° C/0.15 mmHg | $n_D^{20}$ 1.6027 |
| 32 | O | 2-naphthyl | b.p. 154–156° C/0.1 mmHg | $n_D^{20}$ 1.6001 |
| 33 | O | 1-Br-2-naphthyl | | $n_D^{20}$ 1.6248 |
| 34 | O | 1-CH$_3$-2,4-Cl$_2$-naphthyl | b.p. 170–173° C/0.1 mmHg m.p. 46–48° C | |
| 35 | S | C$_6$H$_5$- | b.p. 138–142° C/0.1 mmHg | $n_D^{20}$ 1.6114 |
| 36 | S | 4-Cl-C$_6$H$_4$- | b.p. 147–150° C/0.06 mmHg | $n_D^{20}$ 1.6183 |
| 37 | S | 2,4-Cl$_2$-C$_6$H$_3$- | | $n_D^{20}$ 1.6236 |
| 38 | S | 4-CH$_3$-C$_6$H$_4$- | | $n_D^{20}$ 1.6011 |

EXAMPLE 5

15 parts of compound (28), 80 parts of diatomaceous earth and clay and 5 parts of the emulsifier "RUNNOX" (product of Toho Kagaku Kogyo K.K., Japan) are ground and mixed together to form a wettable powder. It is diluted with water for actual application. [diatomaceous earth and clay (3:2) : "RUNNOX": polyoxythylenealkylarylether]

EXAMPLE 6

30 parts of compound (4), 30 parts of xylene, 30 parts of "KAWAKAZOL" (product of Kawasaki Kasei Kogyo K.K., Japan), and 10 parts of the emulsifier "SORPOL" (product of Toho Kagaku Kogyo K.K., Japan) are mixed with stirring to form an emulsifiable concentration. It is diluted with water for actual application. ["KAWAKAZOL": aliphatic hydrocarbons with high boiling point : "SORPOL": polyoxyethylenealkylarylether]

EXAMPLE 7

10 parts of compound (36), 10 parts of bentonite, 78 parts of talc and 2 parts of lignin sulfonate are formed into a mixture and it is intimately mixed with 25 parts of water. The mixture is finely divided by means of an extruding granulator to give particles of 20–40 mesh, followed by drying at 40°–50° C.

EXAMPLE 8

2 parts of compound No. 17 and 98 parts of a mixture of talc and clay were ground and mixed together to form a dust. [talc and clay (3:1)]

Note: The term "parts" used in the Example (5) to (8) means weight.

EXAMPLE 9

Preparation of Test compound

Solvent: 3 parts by weight of dimethylformamide.
Emulsifier: 0.1 part by weight of alkyl aryl polyglycol ether.

In order to prepare a suitable preparation of an active compound, one part by weight of the active compound is mixed with the above amount of the solvent containing the above amount of the emulsifier, and the mixture is diluted with water to form an aqueous preparation containing the active compound at a prescribed concentration.

Test 1 Test on rice stem borers (*Chilo supperssalis*) larvae

Test procedure

Rice plants of tillering stage in a pot of 12 cm diameter are attached with eggs of rice stem borer. Seven days after hatching, the preparation of the active compound prepared in Example 9 at the prescrived concentration is sprayed in an amount of 40 ml per pot and the pot is then kept in a greenhouse for 3 days. The stems of the so-treated rice plants are examined separately to count the numbers of living insects and dead insects and to calculate the killing ratio.

Test 2 Test on tobacco cutworm (*Prodenia litura*) larvae

Test procedure

Sweet-potato leaves are dipped in a preparation of the active compound prepared in Example 9, and they are dried in air and placed in a 9 cm diameter Petri dish. Then 10 of thirdinstar tobacco cutworm larvae are put into the dish and the dish is kept in a thermostat chamber maintained at 28° C. After 24 hours have passed, the number of the dead larvae is counted and the killing ratio is calculated.

Test 3 Test on almond moth (*Ephestia cautella*)

Test procedure 20 almond-moth mature larvae are put into a wire gauze vessel of 7 cm diameter and 0.9 cm height. The vessel is dipped for 10 seconds in a preparation of the active compound prepared in Example 9 at a prescribed concentration, and then the vessel is allowed to stand for 24 hours in a thermostat chamber. The number of dead larvae is counted and the killing ratio is calculated.

The results of the tests are shown in Table 2 in which results of comparative tests using analogous compounds, designated compounds (A) to (L), are also shown. The entries in the table are killing ratios expressed as percentage values.

Table 2

| Compound | | Active Component Concentration | Harmful Insects | | | | | | |
|---|---|---|---|---|---|---|---|---|---|
| | | | Tobacco cutworm | | | Almond moth | | | rice stem borer |
| | | | 0.1% | 0.03% | 0.01% | 0.1% | 0.03% | 0.01% | 0.03% |
| (A) | 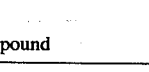 | | 65 | 0 | 0 | 0 | 0 | 0 | 2.5 |
| (B) | 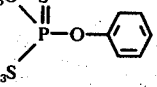 | | 90 | 5 | 0 | 20 | 0 | 0 | 3.1 |
| (1) | 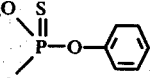 | | 100 | 100 | 100 | 100 | 100 | 100 | 100 |
| (C) | 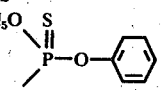 | | 100 | 15 | 0 | 100 | 80 | 15 | 12.3 |

Table 2-continued

| Compound | | Active Component Concentration | Harmful Insects | | | | | | |
|---|---|---|---|---|---|---|---|---|---|
| | | | Tobacco cutworm | | | Almond moth | | | rice stem borer |
| | | | 0.1% | 0.03% | 0.01% | 0.1% | 0.03% | 0.01% | 0.03% |
| (D) | $C_2H_5O$, $C_2H_5S$ / P(=S) - O - (2-Cl,4-Cl phenyl) | | 70 | 10 | 0 | 50 | 0 | 0 | 0 |
| (4) | $C_2H_5O$, $n-C_3H_7S$ / P(=S) - O - (2-Cl,4-Cl phenyl) | | 100 | 100 | 100 | 100 | 100 | 100 | 100 |
| (E) | $C_2H_5O$, $n-C_4H_9S$ / P(=S) - O - (2-Cl,4-Cl phenyl) | | 90 | 45 | 0 | 25 | 0 | 0 | 3.6 |
| (F) | $C_2H_5O$, $C_2H_5S$ / P(=S) - O - (4-SCH$_3$ phenyl) | | 95 | 30 | 0 | 15 | 0 | 0 | 40 |
| (17) | $C_2H_5O$, $n-C_3H_7S$ / P(=S) - O - (4-SCH$_3$ phenyl) | | 100 | 100 | 100 | 100 | 100 | 100 | 100 |
| (G) | $C_2H_5O$, $n-C_4H_9S$ / P(=S) - O - (4-SCH$_3$ phenyl) | | 100 | 80 | 0 | 75 | 0 | 0 | 19.2 |
| (H) | $C_2H_5O$, $C_2H_5S$ / P(=S) - O - (4-Cl phenyl) | | 80 | 0 | 0 | 35 | 0 | 0 | 1.1 |
| (36) | $C_2H_5O$, $n-C_3H_7S$ / P(=S) - S - (4-Cl phenyl) | | 100 | 100 | 100 | 100 | 100 | 100 | 100 |
| (J) | $C_2H_5O$, $n-C_4H_9S$ / P(=S) - S - (4-Cl phenyl) | | 100 | 85 | 5 | 95 | 0 | 0 | 6.5 |
| (K) | $C_2H_5O$, $C_2H_5S$ / P(=S) - O - (4-CN phenyl) | | 80 | 10 | 0 | 60 | 0 | 0 | 3.2 |
| (28) | $C_2H_5O$, $n-C_3H_7S$ / P(=S) - O - (4-CN phenyl) | | 100 | 100 | 100 | 100 | 100 | 100 | 100 |
| (L) | $C_2H_5O$, $n-C_4H_9S$ / P(=S) - O - (4-CN phenyl) | | 100 | 40 | 0 | 100 | 30 | 0 | 15.3 |
| Untreated control | | | | 5 | | | 5 | | 8.2 |

From the results shown in Table 2 it can be seen that phosphoric acid esters of the formula (I) exhibit particularly excellent effects against harmful insects belonging to the Lepidoptera as compared with analogous compounds.

EXAMPLE 10

Test on Tobacco cutworm:

Test Procedure

The test is conducted in the same manner as in Test 2 of Example 9. The results are shown in Table 3.

Table 3

Results of Test of Effect against the Tobacco Cutworm
Killing Ratio (%)

| Compound No. | 1000 ppm | 300 ppm | 100 ppm |
|---|---|---|---|
| 1 | 100 | 100 | 100 |
| 2 | 100 | 100 | 100 |
| 3 | 100 | 100 | 100 |
| 4 | 100 | 100 | 100 |
| 5 | 100 | 100 | 100 |
| 6 | 100 | 100 | 100 |
| 7 | 100 | 100 | 100 |
| 8 | 100 | 100 | 100 |
| 9 | 100 | 100 | 100 |
| 10 | 100 | 100 | 60 |
| 11 | 100 | 100 | 50 |
| 12 | 100 | 96 | 60 |
| 13 | 100 | 100 | 90 |
| 14 | 100 | 90 | 80 |
| 15 | 100 | 100 | 100 |

Table 3-continued

Results of Test of Effect against the Tobacco Cutworm

| Compound No. | Killing Ratio (%) | | |
|---|---|---|---|
| | 1000 ppm | 300 ppm | 100 ppm |
| 16 | 100 | 80 | 50 |
| 17 | 100 | 100 | 100 |
| 18 | 100 | 100 | 100 |
| 19 | 100 | 100 | 90 |
| 20 | 100 | 100 | 100 |
| 21 | 100 | 100 | 100 |
| 22 | 100 | 100 | 100 |
| 23 | 100 | 100 | 100 |
| 24 | 100 | 100 | 100 |
| 25 | 100 | 100 | 100 |
| 26 | 100 | 100 | 100 |
| 27 | 100 | 100 | 100 |
| 28 | 100 | 100 | 100 |
| 29 | 100 | 100 | 100 |
| 30 | 100 | 100 | 100 |
| 31 | 100 | 100 | 100 |
| 32 | 100 | 100 | 90 |
| 33 | 100 | 100 | 100 |
| 34 | 100 | 100 | 77 |
| 35 | 100 | 100 | 100 |
| 36 | 100 | 100 | 100 |
| 37 | 100 | 100 | 80 |
| 38 | 100 | 100 | 60 |
| [1]Sumithion (commercially available comparison) | 100 | 80 | 20 |

Notes:
The compounds numbers in the Table correspond to those in Examples 1, 2 and 3 and Table 1.
[1]Sumithion: O,O-dimethyl-0-(3-methyl-4-nitrophenyl) thiophosphate

EXAMPLE 11

Test on carmine mites imagines (*Tetranychus telarius*)

Test Procedure

A haricot plant having two developing leaves planted in a 6 diameter pot is placed with 50–100 carmine mite imagines and nymphs. Two days after the infection, emulsions containing the active compound at a prescribed concentration, which is prepared in the same manner as in Example 9, is sprayed in an amount of 40 ml per pot. The pot is kept in a greenhouse for 10 days, and the control effect is evaluated. The evaluation is expressed by an index on the following scale:

Index:
- 3: No living image or nymph.
- 2: less than 5% of living imagines and nymphs based on the untreated control
- 1: 5 – 50% of living imagines and nymphs based on the untreated control
- 0: more than 50% of living imagines and nymphs based on the untreated control.

The results are shown in Table 4.

Table 4

Results of tests of effects against carmine mites:

| Compound No. | Control effect index | |
|---|---|---|
| | 300 ppm | 100 ppm |
| 2 | 3 | 2 |
| 3 | 3 | 2 |
| 4 | 3 | 2 |
| 5 | 3 | 2 |
| 6 | 3 | 2 |
| 7 | 3 | 2 |
| 14 | 3 | 2 |
| 17 | 3 | 3 |
| 18 | 3 | 3 |
| 19 | 3 | 2 |
| 23 | 3 | 3 |
| 28 | 3 | 3 |
| 29 | 3 | 2 |
| 31 | 3 | 2 |
| 32 | 3 | 1 |
| 35 | 3 | 2 |

Table 4-continued

Results of tests of effects against carmine mites:

| Compound No. | Control effect index | |
|---|---|---|
| | 300 ppm | 100 ppm |
| 36 | 3 | 2 |
| Phenkaptone[1](commercially available comparison) | 3 | 1 |
| CPCBS[2](commercially available comparison) | 2 | 0 |

Notes:
The compound numbers in the Table correspond to those in Examples 1, 2 and 3 and Table 1.
Phenkaptone[1]: O,O-diethyl-S-(2,5-dichlorophenylmercaptomethyl) dithiophosphate
CPCBS[2]: p-chlorophenyl-p'-chlorobenzenesulfonate

EXAMPLE 12

Test on green peach aphids (*Myzus persica*)

Test Procedure

A sweet-potato leaf is dipped in an emulsion containing the active compound at a prescribed concentration, which is prepared in the same manner as in Example 9 and dried in air. Then the leaf is placed in a Petri dish of 9 cm diameter and 20 grams peach aphids are placed therein. Then the dish is kept for 24 hours in a thermostat chamber maintained at 28° C. Then the number of the dead aphids is counted and the killing ratio is calculated.

The results are shown in Table 5.

Table 5

Effects against green peach aphids:

| Compound No. | Killing Ratio (%) | |
|---|---|---|
| | 100 ppm | 10 ppm |
| 3 | 100 | 92.3 |
| 4 | 100 | 97.6 |
| 17 | 100 | 98.7 |
| 18 | 100 | 89.5 |
| 23 | 100 | 91.5 |
| 28 | 99.2 | 90.5 |
| 36 | 100 | 91.3 |
| Disyston[1] (commercially available comparison) | 98.5 | 76.7 |
| Parathion[2] (commercially available comparison) | 99.4 | 87.8 |

Notes:
The compound numbers in the Table correspond to those in Examples 1, 2 and 3 and Table 1.
Disyston[1]: O,O-diethyl-S-2(ethylthio)phosphorodithioate
Parathion[2]: O,O-diethyl-p-nitrophenyl-thiophosphate

EXAMPLE 13

Preparation of test compound 2 parts by weight of an active compound is mixed with 98 parts by weight of talc, and the mixture is ground to form a dust.

Test on root knot nematode disease (*Meloidogyne hapla*)

Test Procedure

The so-prepared dust is mixed with soil tainted with sweet-potato root knot nematodes in an amount such that a prescribed concentration of the active compound is attained in the soil. The treated soil is uniformly stirred and mixed, and then it is packed into pots each having an area of 1/5000 are. About 20 tomato seeds (Kurihara variety) are sowed per pot and cultivated for 4 weeks in a greenhouse. Each root is then drawn out from the soil without harming it. The damage degree is evaluated as the average of 10 roots for each group, based on the following scale.

| Damage Degree | |
|---|---|
| 0 | no knot (perfect control) |
| 1 | knots are formed slightly |
| 2 | knots are formed appreciably |
| 3 | knots are formed considerably |
| 4 | formation of knots is extreme (same as in untreated control). |

The knot index is determined by the following equation:

$$\text{Knot Index} = \frac{\Sigma \text{ (rank value)} \times \text{(rank population)} \times 100}{\text{(whole population examined)} \times 4}$$

The results are shown in Table 6.

Table 6

Effects against root knot nematodes:

| Compound No. | Knot Index (%) | | |
|---|---|---|---|
| | 100 ppm | 30 ppm | 10 ppm |
| 4 | 0 | 0.8 | 5.9 |
| 5 | 0 | 0 | 0.9 |
| 17 | 0 | 0 | 1.3 |
| 20 | 0 | 0.2 | 1.1 |
| 28 | 0 | 0.7 | 8.6 |
| 36 | 0 | 0.3 | 12.3 |
| VC[1] (commercially available comparison | 0 | 0.8 | 25.4 |

Notes: The compound numbers in the Table correspond to those in Examples 1, 2 and 3 and Table 1.
VC[1]: O,O-diethyl-O-dichlorophenylthiophosphate.

It will be appreciated that the instant specification and examples are set forth by way of illustration and not limitation, and that various modifications and changes may be made without departing from the spirit and scope of the present invention.

What is claimed is:

1. An insecticidal, acaricidal and nematocidal composition comprising an insecticidally, acaricidally, or nematocidally effective amount of a phosphoric acid ester of the formula $$\begin{array}{c} C_2H_5O \\ \diagdown \\ n\text{-}C_3H_7S \end{array} \overset{S}{\underset{\|}{P}}\!\!-\!X\!-\!Z$$

in which
X is an oxygen or sulfur atom,
Z is a group of the formula

[phenyl with Ym substituents or naphthyl with Ym substituents]

Y is a halogen atom or a lower alkyl, lower alkoxy, lower alkylmercapto, lower alkyl-sulfinyl, nitro, cyano or phenyl group, and at least one Y is lower alkoxy, lower alkyl-mercapto, lower alkyl-sulfinyl, nitro or cyano, and
m is 1 or 2,
in admixture with a diluent.

2. The composition according to claim 1 in which the active compound is:
O-ethyl-O-(4-methylmercaptophenyl)-S-n-propyl-phosphorothionothiolate,
O-ethyl-O-(3-methyl-4-methylmercaptophenyl)-S-n-propylphosphorothionothiolate,
O-ethyl-O-(4-methylsulfinylphenyl)-S-n-propyl-phosphorothionothiolate,
O-ethyl-O-(4-nitrophenyl)-S-n-propyl-phosphorothionothiolate, or
O-ethyl-O-(4-cyanophenyl)-S-n-propyl-phosphorothionothiolate.

3. A method of combating insects, acarids and nematodes which comprises applying to the insects, acarids, nematodes or a habitat thereof an insecticidally, acaricidally or nematocidally effective amount of a phosphoric acid ester of the formula $$\begin{array}{c} C_2H_5O \\ \diagdown \\ n\text{-}C_3H_7S \end{array} \overset{S}{\underset{\|}{P}}\!\!-\!X\!-\!Z$$

in which
X is an oxygen or sulfur atom,
Z is a group of the formula

[phenyl with Ym substituents or naphthyl with Ym substituents]

Y is a halogen atom or a lower alkyl, lower alkoxy, lower alkylmercapto, lower alkylsulfinyl, nitro, cyano or phenyl group, and at least one Y is lower alkoxy, lower alkylmercapto, lower alkyl-sulfinyl, nitro or cyano, and
m is 1 or 2.

4. The method according to claim 3 in which at least one Y is a nitro or cyano group or a $C_1$–$C_4$ alkoxy, $C_1$–$C_4$ alkylmercapto, or $C_1$–$C_4$ alkylsulfinyl group.

5. The method according to claim 3 wherein such compound is O-ethyl-O-(4-methylmercaptophenyl)-S-n-propyl-phosphorothionothiolate of the formula $$\begin{array}{c} C_2H_5O \\ \diagdown \\ n\text{-}C_3H_7S \end{array} \overset{S}{\underset{\|}{P}}\!\!-\!O\!-\!\!\!\bigcirc\!\!\!-\!SCH_3$$

6. The method according to claim 3 wherein such compound is O-ethyl-O-(3-methyl-4-methylmercaptophenyl)-S-n-propyl-phosphorothionothiolate of the formula $$\begin{array}{c} C_2H_5O \\ \diagdown \\ n\text{-}C_3H_7S \end{array} \overset{S}{\underset{\|}{P}}\!\!-\!O\!-\!\!\!\bigcirc\!\!\!\overset{CH_3}{\underset{S-CH_3}{}}$$

7. The method according to claim 3 wherein such compound is O-ethyl-O-(4-methylsulfinylphenyl)-S-n-propyl-phosphorothionothiolate of the formula

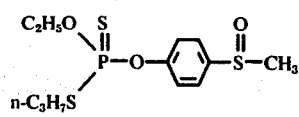
8. The method according to claim 3 wherein such compound is O-ethyl-O-(4-nitrophenyl)-S-n-propyl-phosphorothionothiolate of the formula
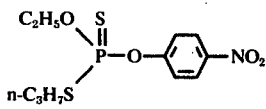
9. The method according to claim 3 wherein such compound is O-ethyl-O-(4-cyanophenyl)-S-n-propyl-phosphorothionothiolate of the formula
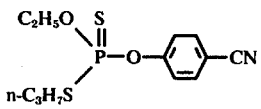
* * * * *